(12) United States Patent
Almeflo

(10) Patent No.: US 11,369,521 B2
(45) Date of Patent: Jun. 28, 2022

(54) EARMUFF HEARING-PROTECTION DEVICE COMPRISING SOUND-ATTENUATING MEMBERS

(71) Applicant: 3M INNOVATIVE PROPERTIES COMPANY, St. Paul, MN (US)

(72) Inventor: Per Ove Almeflo, Ramlösa (SE)

(73) Assignee: 3M Innovative Properties Company, St. Paul, MN (US)

( * ) Notice: Subject to any disclaimer, the term of this patent is extended or adjusted under 35 U.S.C. 154(b) by 426 days.

(21) Appl. No.: 16/484,693

(22) PCT Filed: Feb. 15, 2018

(86) PCT No.: PCT/IB2018/050933
§ 371 (c)(1),
(2) Date: Aug. 8, 2019

(87) PCT Pub. No.: WO2018/150351
PCT Pub. Date: Aug. 23, 2018

(65) Prior Publication Data
US 2020/0000639 A1 Jan. 2, 2020

Related U.S. Application Data

(60) Provisional application No. 62/459,768, filed on Feb. 16, 2017.

(51) Int. Cl.
*A61F 11/14* (2006.01)
(52) U.S. Cl.
CPC .................................. *A61F 11/14* (2013.01)

(58) Field of Classification Search
CPC . A61F 11/14; A61F 11/06; H04R 1/10; H04R 1/1008; H04R 1/1083; H04R 1/1091
See application file for complete search history.

(56) References Cited

U.S. PATENT DOCUMENTS

| | | | |
|---|---|---|---|
| 1,312,493 A | 8/1919 | Theis | |
| 1,483,366 A | 2/1924 | Mazer | |
| 3,432,861 A | 3/1969 | Flagg | |
| 3,875,592 A | 4/1975 | Aileo | |
| 3,922,725 A * | 12/1975 | Csiki | A61F 11/14 2/209 |
| 4,924,976 A | 5/1990 | Bernett | |

(Continued)

FOREIGN PATENT DOCUMENTS

| | | |
|---|---|---|
| CN | 102475599 A | 5/2012 |
| CN | 105662708 | 6/2016 |

(Continued)

OTHER PUBLICATIONS

International Search Report for PCT International Application No. PCT/IB2018-050933, dated May 29, 2018, 6pgs.

*Primary Examiner* — Edgardo San Martin
(74) *Attorney, Agent, or Firm* — Kenneth B. Wood

(57) ABSTRACT

An earmuff hearing-protection device (1) including a non-porous, sound-attenuating body (50) disposed within an interior space (31) defined by a shell (30) of an earmuff of the device, the non-porous, sound-attenuating body including sound-attenuating members (100) arranged and spaced to define a set of high aspect ratio air gaps (e.g. 300) between major side surfaces of neighboring members.

19 Claims, 9 Drawing Sheets

(56) References Cited

U.S. PATENT DOCUMENTS

| | | | |
|---|---|---|---|
| 5,241,971 A * | 9/1993 | Lundin | A61F 11/14 |
| | | | 128/864 |
| 5,815,842 A | 10/1998 | Hiselius | |
| 5,996,123 A | 12/1999 | Leight | |
| 6,290,022 B1 | 9/2001 | Wolf | |
| 6,353,938 B1 * | 3/2002 | Young | A61F 11/14 |
| | | | 181/129 |
| 7,198,133 B2 * | 4/2007 | Warring | A61B 5/121 |
| | | | 181/129 |
| 7,444,687 B2 | 11/2008 | Sato | |
| 7,703,572 B2 * | 4/2010 | Du | A61F 11/14 |
| | | | 181/129 |
| 7,717,226 B2 * | 5/2010 | Purcell | A61F 11/14 |
| | | | 181/129 |
| 7,853,034 B1 * | 12/2010 | Gresko | H04R 5/033 |
| | | | 381/372 |
| 8,302,731 B2 | 11/2012 | Nilsson | |
| 9,744,078 B2 * | 8/2017 | Carolan | A61F 11/14 |
| 10,080,077 B2 * | 9/2018 | Silvestri | H04R 1/288 |
| 11,026,843 B2 * | 6/2021 | Werner | A61F 11/14 |
| 2009/0232324 A1 | 9/2009 | Zwislocki | |
| 2011/0225705 A1 | 9/2011 | Fernandes | |
| 2013/0153328 A1 | 6/2013 | Carolan | |
| 2020/0396532 A1 * | 12/2020 | Bui | A61B 5/0006 |
| 2022/0062056 A1 * | 3/2022 | Jenkins | G10K 11/162 |

FOREIGN PATENT DOCUMENTS

| | | | |
|---|---|---|---|
| CN | 108836631 A | * | 11/2018 |
| EP | 3228290 | | 10/2017 |
| SE | 450546 B | * | 7/1987 |
| WO | WO 1994-17763 | | 8/1994 |
| WO | WO 2005-072668 | | 8/2005 |

* cited by examiner

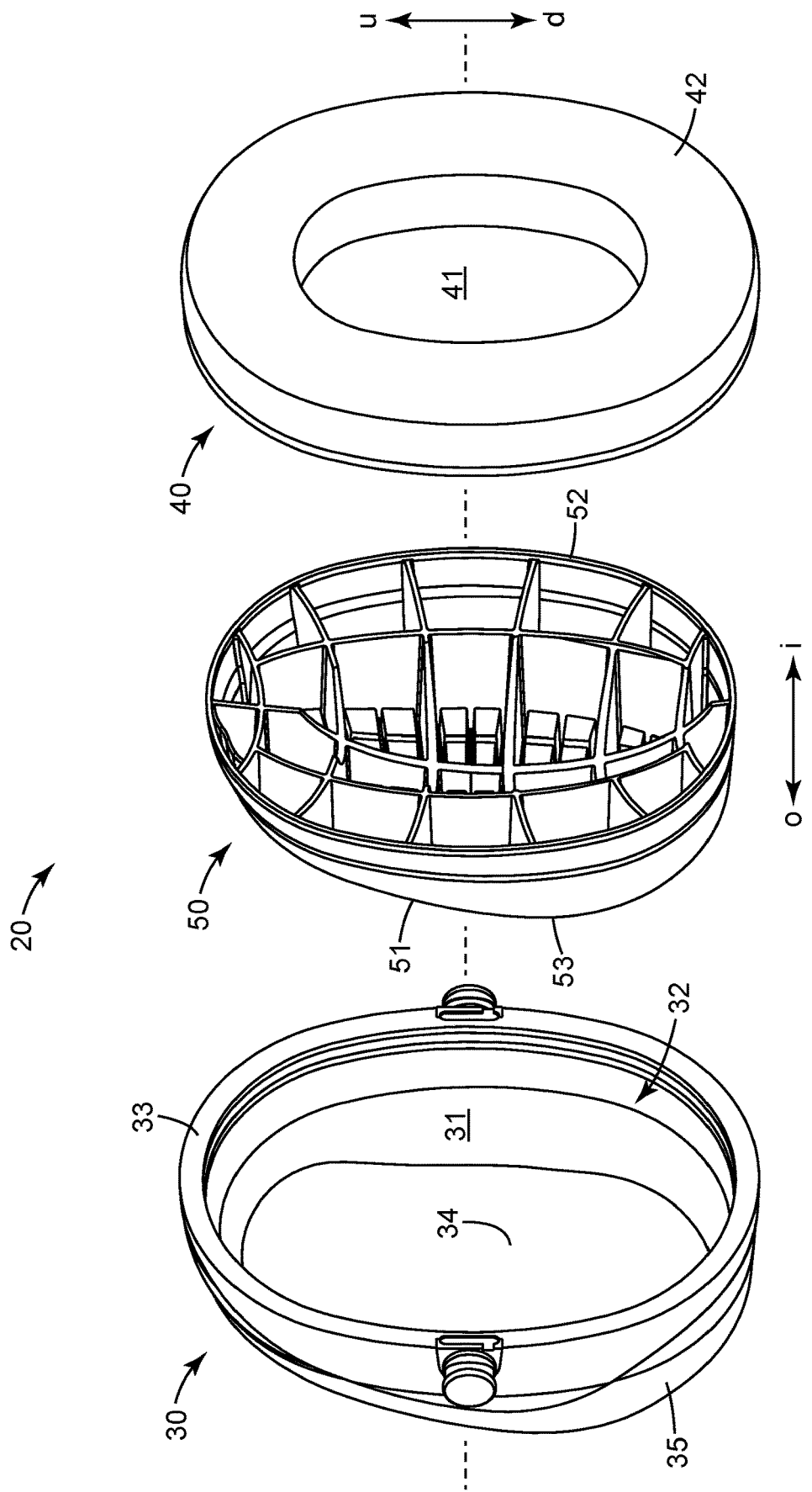

EARMUFF HEARING-PROTECTION DEVICE COMPRISING SOUND-ATTENUATING MEMBERS

BACKGROUND

Earmuff hearing-protection devices are widely used for protecting individuals from e.g. environmental or workplace noise. Typically such devices include a pair of cup-shaped shells fastened to a headband, helmet or other headpiece. To each shell is typically fitted an ear-encircling sealing ring to improve comfort and to seal the shell against the side of a wearer's head. An interior space defined by the shell typically includes a sound absorber to enhance the functioning of the hearing-protection device; such sound absorbers are typically comprised of porous materials such as open-celled foams, fibrous materials, or the like.

SUMMARY

In broad summary, herein is disclosed an earmuff hearing-protection device comprising a non-porous, sound-attenuating body disposed within an interior space defined by a shell of an earmuff of the device, the non-porous, sound-attenuating body comprising sound-attenuating members arranged and spaced to define a set of high aspect ratio air gaps between major side surfaces of neighboring members. These and other aspects will be apparent from the detailed description below. In no event, however, should this broad summary be construed to limit the claimable subject matter, whether such subject matter is presented in claims in the application as initially filed or in claims that are amended or otherwise presented in prosecution.

BRIEF DESCRIPTION OF THE DRAWINGS

FIG. 2 is a side perspective exploded view of an exemplary earmuff of an earmuff hearing-protection device.

FIG. 3b is another side view of the exemplary non-porous, sound attenuating body of FIG. 3a.

FIG. 3c is another side view of the exemplary non-porous, sound attenuating body of FIG. 3a.

Like reference numbers in the various figures indicate like elements. Some elements may be present in identical or equivalent multiples; in such cases only one or more representative elements may be designated by a reference number but it will be understood that such reference numbers apply to all such identical elements. All figures and drawings in this document are to scale.

As used herein, the term "inward" refers to a direction generally toward the sagittal plane of the head of a person wearing the herein-disclosed hearing-protection device. The term "outward" refers to a direction generally away from the sagittal plane; inward and outward directions are indicated on various Figures herein. Terms such as "upward" and "downward", "vertical" and "horizontal", "above" and "below", and the like, have their customary meaning as applied to a person wearing the hearing-protection device with their head in an upright position. The term "longitudinal" denotes the long axis of an earmuff and of a non-porous sound-attenuating body thereof; typically, when the hearing-protection device is worn by a user, the longitudinal axis of the earmuff will at least generally coincide with the vertical direction of the earmuff and of the hearing-protection device.

As used herein as a modifier to a property or attribute, the term "generally", unless otherwise specifically defined, means that the property or attribute would be readily recognizable by a person of ordinary skill but without requiring a high degree of approximation (e.g., within +/−20% for quantifiable properties). The term "substantially", unless otherwise specifically defined, means to a high degree of approximation (e.g., within +/−10% for quantifiable properties). The term "essentially" means to a very high degree of approximation (e.g., within plus or minus 2% for quantifiable properties); it will be understood that the phrase "at least essentially" subsumes the specific case of an "exact" match. However, even an "exact" match, or any other characterization using terms such as e.g. same, equal, identical, uniform, constant, and the like, will be understood to be within the usual tolerances or measuring error applicable to the particular circumstance rather than requiring absolute precision or a perfect match. Those of ordinary skill will appreciate that as used herein, terms such as "essentially free of", and the like, do not preclude the presence of some extremely low, e.g. 0.1% or less, amount of material, as may occur e.g. when using large scale production equipment subject to customary cleaning procedures. All references herein to numerical parameters (dimensions, ratios, and so on) are understood to be calculable (unless otherwise noted) by the use of average values derived from a number of measurements of the parameter.

DETAILED DESCRIPTION

Figure 1:
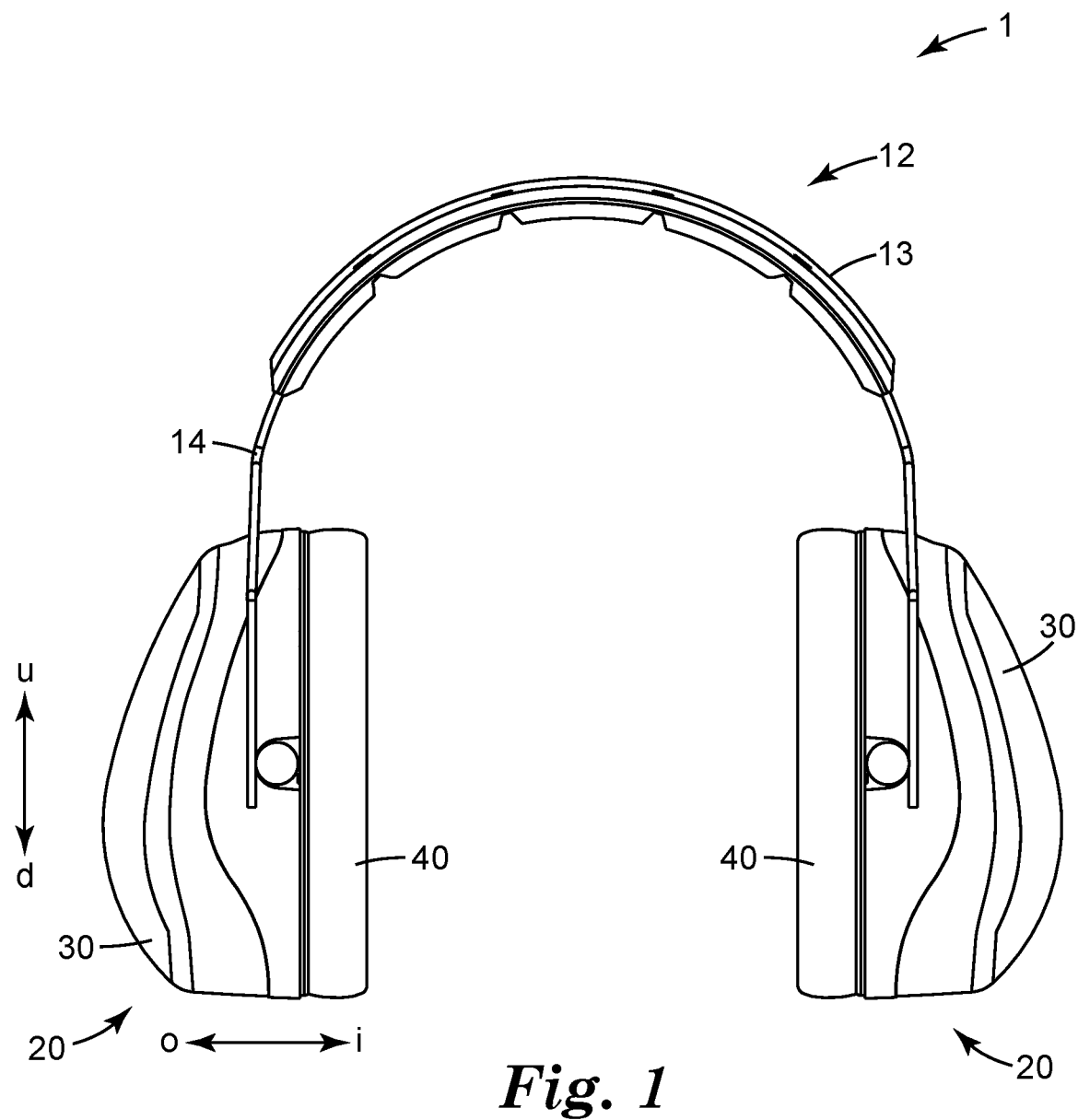
FIG. 1 is a front view of an exemplary earmuff hearing-protection device comprising first and second earmuffs affixed to a headband.

Disclosed herein is an earmuff hearing-protection device 1. As shown in exemplary embodiment in FIG. 1, such a hearing-protection device includes a headpiece 12 e.g. in the form of a headband comprising supports 14 to which are attached first and second (e.g. left and right) earmuffs 20. In many convenient embodiments, supports 14 may be inwardly biased to hold the earmuffs securely against the sides of the head of a user, and headpiece 12 may include a pad 13 for enhanced comfort. The ends of supports 14 may be detachably or non-detachably connected (by any suitable connector, not shown in FIG. 1) to earmuffs 20.

As shown in exemplary embodiment in FIG. 2, an earmuff 20 may comprise an outer, molded shell 30. Such a shell is often substantially rigid (e.g., made of a suitable injection-molded polymeric material) so as to minimize the transmission of sound waves therethrough. Shell 30 is generally cup-shaped with a closed outward end 35 and with an open inward end 32 defined by inward rim 33, so that shell 30 defines an interior space (cavity) 31 that is open-ended and inwardly-facing. In many embodiments, an ear-encircling sealing ring 40 that defines a through-passage 41 is affixed (either detachably or non-detachably) to inward rim 33 of shell 30. Sealing ring 40 may be resilient and conformable to provide a comfortable fit and to minimize any leakage of sound between inward surface 42 of cushion 40, and the side of the wearer's head, when hearing-protection device 1 is worn by a wearer.

In some convenient embodiments ear-encircling sealing ring 40 may take the form of a conformable cushion (e.g., of the general design shown in FIG. 2) with a composite construction including a generally impervious outer cover and a resilient interior made of e.g. foam. Such a cushion may be made from a variety of materials that will be familiar to persons having ordinary skill in the art, such as the rubber-like cover material and slow recovery polyurethane foam interior described in U.S. Pat. No. 5,996,123. In other embodiments, ear-encircling sealing ring 40 may take the form of a body made of a resilient material and comprising one or more circumferential flanges or lamella, e.g. as described in U.S. Pat. No. 8,302,731. It will thus be appreciated that the term sealing ring is used broadly and can encompass any suitable structure or design. Inward rim 33 of shell 30, and/or sealing ring 40 may have any suitable shape and can respectively define an open end 32 and an ear-encircling orifice 41 having any suitable shape including, e.g., circular, oval, elliptical, round, square or rectangular. Accordingly, it will be understood that the use of terms such as "ear-encircling" and "ring" do not require that sealing "ring" 40 (nor inward rim 33 of shell 30) must necessarily be exactly circular or that it must even exhibit one or more axes of symmetry.

As disclosed herein, earmuffs 20 each comprise a non-porous, sound-attenuating body 50 disposed within interior space 31 defined by shell 30, as shown in exemplary embodiment in FIG. 2. By non-porous is meant that body 50 is comprised of a material that exhibits a density of at least about 0.8 g/cc; the term non-porous excludes materials such as polymeric foams (e.g. foam rubber, polyurethane foam, and the like) and fibrous materials (e.g. webs, blankets or slabs made non-woven organic polymeric fibers, fiberglass and the like). In many convenient embodiments, body 50 will be made of an organic polymeric material, e.g. with a density of at least about 0.85, 0.90, 0.95, 1.00, 1.05, or 1.10 g/cc. Such a material may be shaped (e.g. molded) to form body 50 in any suitable manner. Any suitable organic polymeric material (e.g. a molding resin) may be used, whether thermoplastic or thermoset, and may be chosen from e.g. polyurethane (polyurethane), polypropylene, polyethylene, polystyrene, polyvinylchloride, polyvinylidene chloride, polyester, polyamide, polyoxymethylene, silicone polymers, acrylonitrile-butadiene-styrene polymers, polyphthalamide, and so on. Mixtures, copolymers, and/or blends of any of these may be used. Any such material may include various additives, e.g. fillers, reinforcing agents, antioxidants, colorants and pigments, and so on. Such a material may be shaped to form a non-porous, sound-attenuating body by any suitable means, e.g. injection molding, vacuum molding, gravity-assisted molding, slush molding, and so on. In some embodiments, the entirety, or a portion, of body 50 may be made by an additive manufacturing process (often referred to as 3-D printing), using any organic polymeric resin suitable for such processing. In various embodiments, the material of body 50 may exhibit (e.g. after cooling to room temperature if a thermoplastic material; after curing and cooling if a thermoset material) a Shore A hardness that is less than about 100, 90, 80, 75, 70, or 65, and/or a Shore A hardness that is greater than about 30, 40, 50, 55, 60, 65, 70, or 80.

As shown in FIG. 2, non-porous, sound-attenuating body 50 may include an outward base 51 that provides a generally outward portion of body 50 and that comprises outward surface 53. Base 51 may comprise portions that extend generally inward to terminate at inward rim 52, also as shown in FIG. 2. Base 51 may be shaped to generally match the shape of shell 30; in particular, at least some portions of outward surface 53 of base 51 may be at least substantially congruent with inward surface 34 of shell 30. This can allow that base 51 may be securely held within interior space 31 of shell 30 and in particular can be closely abutted against (e.g., in intimate contact with) inward surface 34 of shell 30. In some embodiments, body 50 may be detachably disposed within interior space 31 of shell 30 so that body 50 may be removed if desired. In such embodiments, body 50 may be e.g. snapped into place by way of complementary features provided e.g. on or near rims 52 and 33 of body 50 and shell 30. Or, body 50 may be held in place within interior space 31 by the affixing of cushion 40 to rim 33 of shell 30. In other embodiments, body 50 may be non-detachably disposed within interior space 31, meaning that body 50 cannot be removed without unacceptably damaging or destroying one or more of body 50, shell 30, or cushion 40. In such embodiments, body 50 may be e.g. adhesively bonded to shell 30, or may be attached thereto by any other suitably permanent means (e.g. by solvent-welding, ultrasonic-welding, and so on).

Figure 8A:
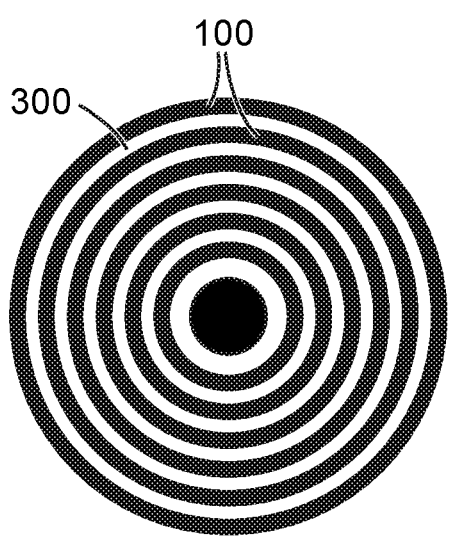
FIG. 8a depicts a plan view, along an inward-outward axis, of an exemplary set of sound-attenuating members.
Figure 8B:
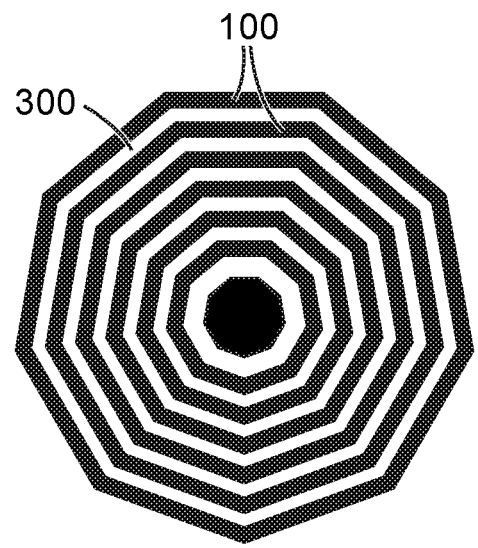
FIG. 8b depicts a plan view, along an inward-outward axis, of another exemplary set of sound-attenuating members.

Non-porous, sound-attenuating body 50 comprises a set of sound-attenuating members 100 that extend at least generally inwardly from outward base 51. By sound-attenuating is meant that body 50 increases the sound-attenuating performance of earmuff 20 over the performance of earmuff 20 in the absence of body 50, as manifested by an increase in Insertion Loss of at least 2 dB over at least one octave that at overlaps (e.g. falls within) the range of 1000-8000 Hz. By way of specific example, the Working Example sound-attenuating body prototypes characterized in FIG. 8 exhibit an increase in Insertion Loss (in some cases of 10 dB or more) over the range of approximately 3.5 kHz to 8 kHz. By a sound-attenuating member is meant a member that contributes to the sound-attenuating achieved by body 50, whether such attenuation is achieved e.g. by facilitating frictional absorption of airborne sound, by reducing sound transmission through solid material, by vibration-damping, by some other mechanism, or by any combination of any such mechanism(s). (Possible sound-attenuating mechanisms that may be present in various circumstances, are discussed in detail later herein.)

In some embodiments, non-porous, sound-attenuating body 50, including outward base 51 and at least some sound-attenuating members 100 thereof, is an integral body. In other words, in such embodiments body 50 and at least some sound-attenuating members thereof are portions of a single, unitary, integral piece (e.g. a molded piece) of organic polymeric resin. However, this does not exclude the possibility of one or more ancillary items (e.g. fasteners, spacers, or the like) being made separately and then attached to body 50. In fact, one or more items that perform at least some sound attenuation can be made separately and then attached to body 50, as long as body 50 comprises a set (i.e. at least two) of sound-attenuating members that are integral with base 51 of body 50.

The inwardly-extending, sound-attenuating members 100 of body 50 may take any suitable form. In various embodiments, inwardly-extending, sound-attenuating members may take the form of e.g. columns, elongated ribs, or a mixture of both, as long as such members are arranged and spaced so as to define high aspect ratio air gaps between major side surfaces of neighboring members, as discussed in detail later herein.

In some embodiments, at least some sound attenuating members 100 of body 50 may take the form of elongated ribs. By elongated ribs are meant structures that extend (e.g., extend integrally) from outward base 51 of body 50 in an at least generally inward direction, and that exhibit a ratio of their longest dimension (e.g. their length) to their shortest dimension (e.g. their width or thickness) of 10:1 or more. In various embodiments, such elongated ribs may exhibit a longest/shortest dimension ratio of at least about 15:1, 20:1, 25:1, or 30:1.

Figure 3A:
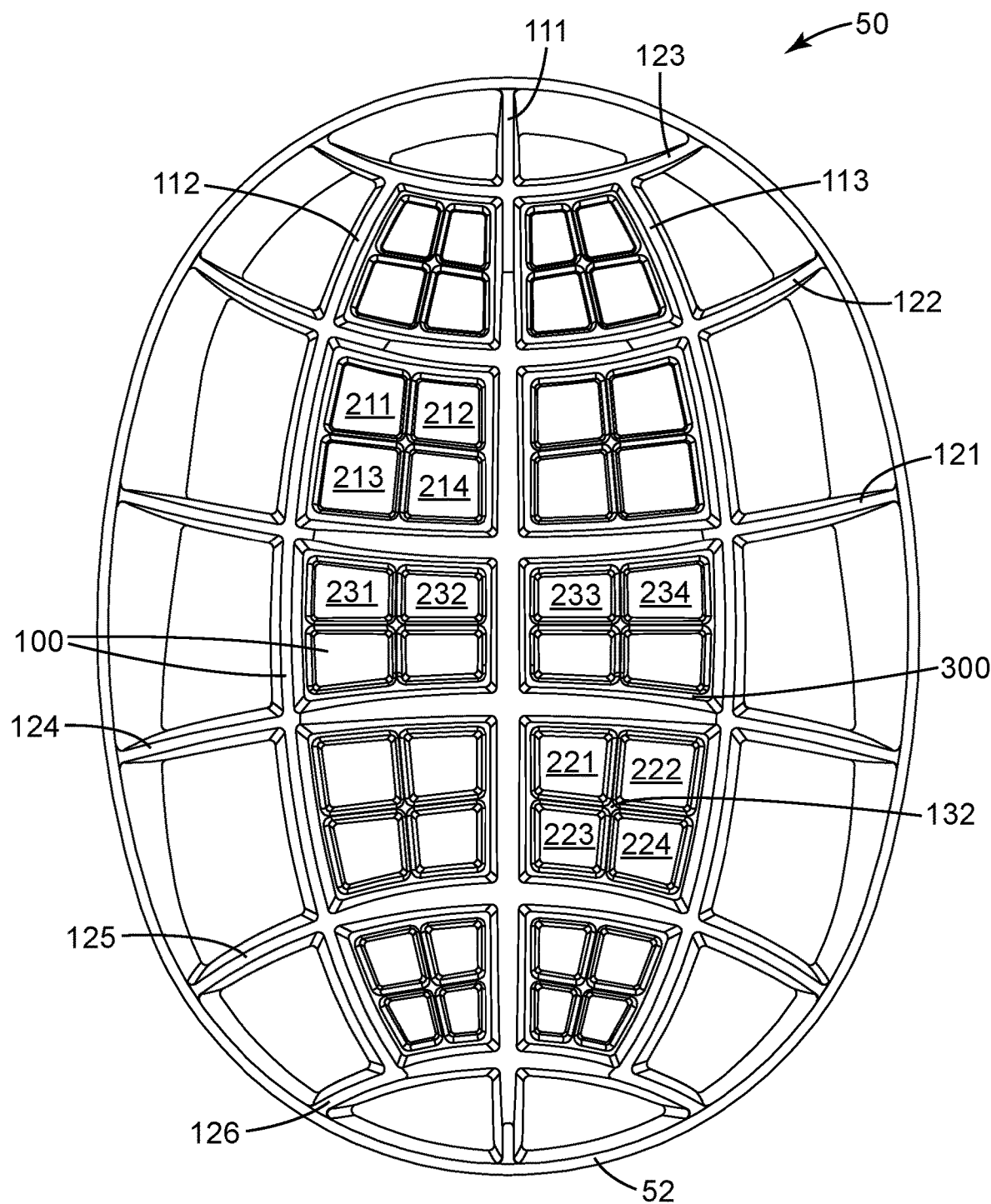
FIG. 3a is a side view of an exemplary non-porous, sound attenuating body of an earmuff of an earmuff hearing-protection device.
Figure 3B:
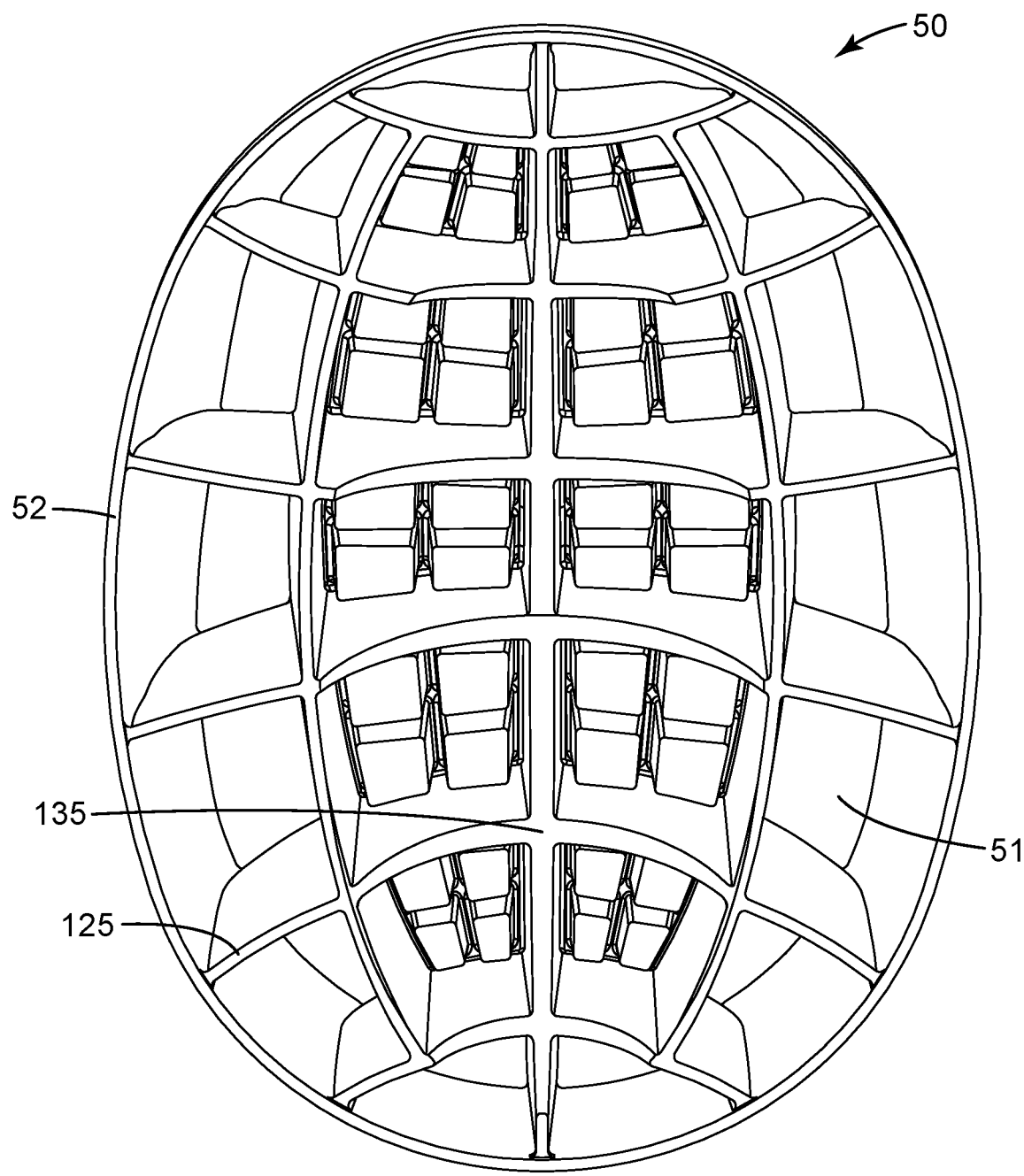
Figure 3C:
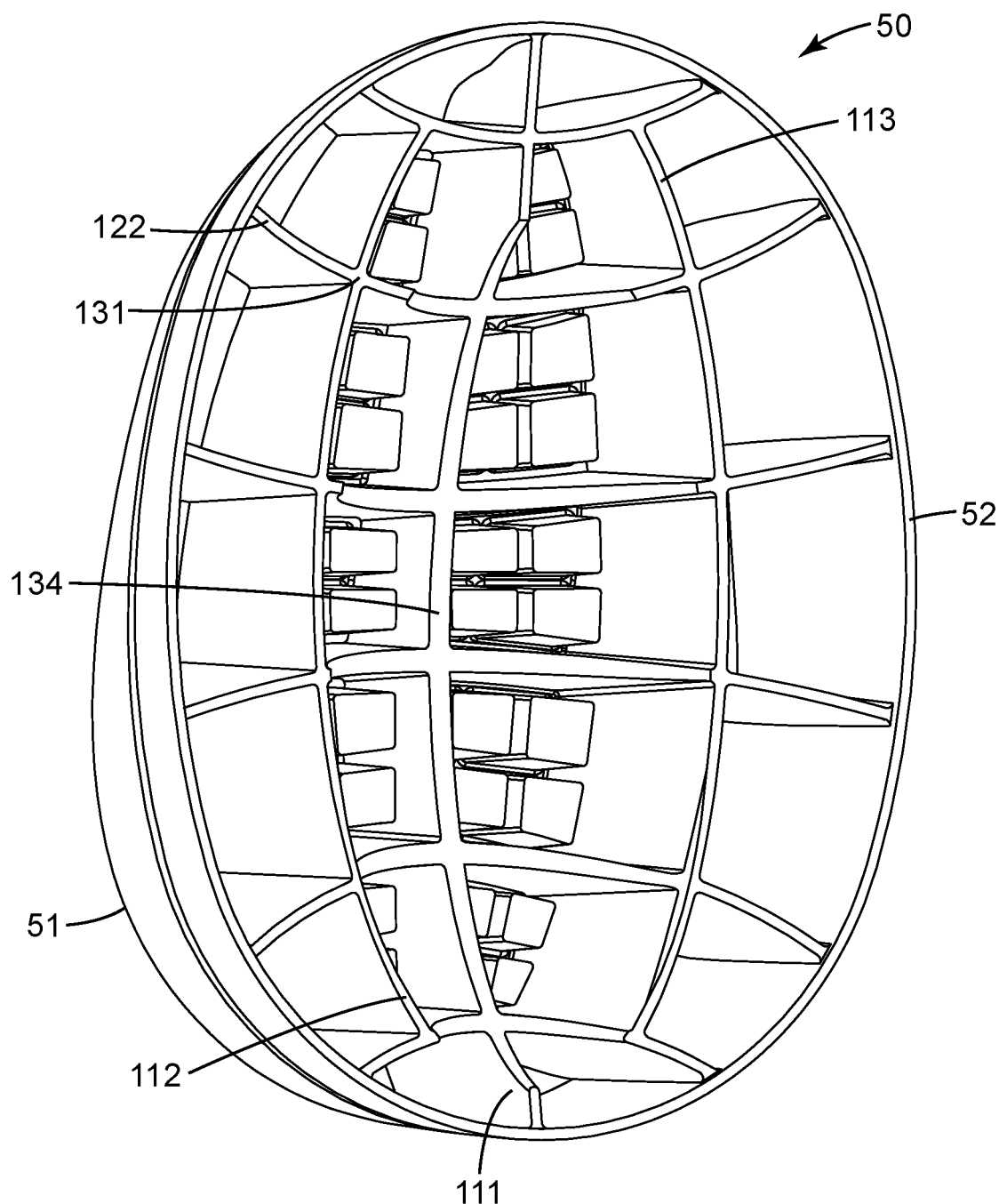
Figure 4:
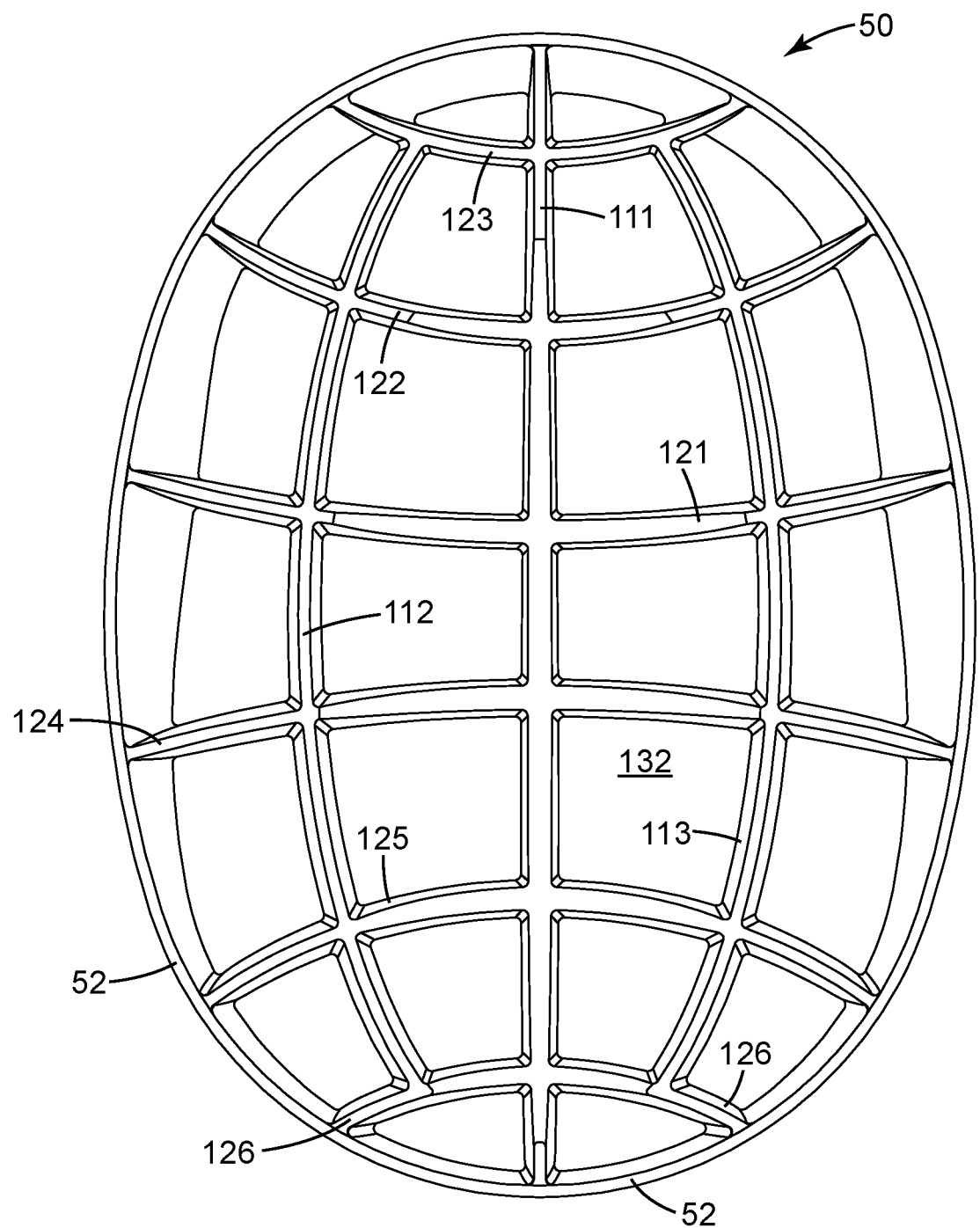
FIG. 4 is another side of side view of an exemplary non-porous, sound attenuating body of FIG. 3a, with a rearward portion of the body being omitted.

Various exemplary ribs are visible in FIG. 3*a*, which is a side view looking outward toward sound-attenuating body 50 along an inward-outward axis of body 50. In FIG. 3*a*, a first set of longitudinal ribs 111, 112, and 113, and a second set of lateral ribs 121, 122, 123, 124, 125, and 126 are depicted (it is evident from FIG. 3*a* that longitudinal ribs and lateral ribs are not required to be oriented in a strictly longitudinal direction or a strictly lateral direction, nor are they required to be strictly linear.) FIGS. 3*b* and 3*c* are similar views but are rotated to slightly different viewing angles so that various ribs and features thereof can be more easily viewed. FIG. 4 is depicted from a similar viewing angle as FIG. 3*a*, but with the outward portion (including most of base 51 and various columns as discussed later) of body 50 omitted so that the ribs can be more clearly seen. As is evident from these Figures, in some embodiments at least some of the ribs can intersect with other ribs; for example, FIG. 3*c* identifies intersection 131 of lateral rib 122 with longitudinal rib 112. Rib intersection 131, and many other rib intersections depicted in these Figures, are "smooth" intersections, meaning that each rib enters and exits the intersection without any offset between the entering and exiting rib portions. However, in some embodiments a rib may exhibit a slight, or even a significant, offset at intersections. In many embodiments at least some longitudinal ribs (e.g. rib 111 as depicted in FIG. 3*c*) may extend along the entire longitudinal length of body 50. Or, e.g. even if offset is present at rib intersections, a set of longitudinal rib segments may collectively extend along the entire longitudinal length of body 50. Similarly, in some embodiments at least some lateral ribs (e.g., ribs 121 and 124), or a set of rib segments, may extend along the entire lateral length of body 50 (at a given longitudinal location of body 50).

In some embodiments, longitudinal and lateral ribs may intersect so as to collectively define a set of compartments (spaces or areas) of base 51 of body 50. In particular embodiments such compartments may be bounded by two longitudinal ribs and two lateral ribs (one such compartment 132, bounded by longitudinal ribs 111 and 113 and by lateral ribs 124 and 125, is identified in FIGS. 3*a* and 4). In some embodiments, any such compartment may by occupied by at least two sound-attenuating members e.g. in the form of inwardly-extending columns, as discussed later.

In some embodiments, at least some ribs of the first set of longitudinal ribs may be arcuate and convex with respect to a longitudinal centerline of body 50. That is, such ribs may be bowed outward from the longitudinal centerline of body 50 in the manner depicted e.g. in FIG. 4, in which longitudinal ribs 112 and 113 are both bowed outward from rib 111 (which lies along the longitudinal centerline of body 50). In some embodiments, at least some ribs of the second set of lateral ribs may be arcuate and concave with respect to a lateral centerline of body 50. That is, such ribs may be bowed inward toward the lateral centerline in the manner depicted e.g. in FIG. 4, in which lateral ribs 121 and 125 are both bowed inward from the lateral centerline (which centerline is not identified in FIG. 4 but which lies between lateral ribs 121 and 124).

In some embodiments, at least some of the ribs may exhibit an outwardly-concave profile, meaning that sections of the rib toward the middle of its elongate length, exhibit an inward surface that is the maximally-outwardmost surface of the rib. By way of specific example, longitudinal rib 111 as shown in FIG. 3*c* exhibits an outwardly-concave profile with location 134 of rib 111 being a maximally-outward location of the inward surface of rib 111. Similarly, rib 125 as shown in FIG. 3*b* also exhibits an outwardly-concave profile with location 135 of lateral rib 125 being a maximally-outward location of the inward surface of rib 125. It will be appreciated that in the exemplary design of FIGS. 3*a*-3*c*, several ribs (longitudinal rib 111, and lateral ribs 121, 122, 124, 125 and 126) exhibit outwardly-concave profiles. It will be appreciated that such arrangements can allow the elongated ribs to serve their desired functions (as discussed in detail later herein) while providing that at least some (e.g. central) sections of the ribs are recessed outward so that these sections of the ribs do not unacceptably contact (e.g. put pressure on) the pinna of a wearer of the hearing-protection device.

In some embodiments at least some sound attenuating members 100 of body 50 may take the form of inwardly-extending columns. Exemplary columns (all numbered with reference numerals in the 200*s*) are identified by number e.g. in FIGS. 3*a*, 5, 6 and 7, but it will be understood that many more columns are depicted in the Figures herein. (For example, forty columns, in ten groups of four, are visible in FIG. 3*a*.) By columns are meant structures that extend (e.g., extend integrally) from outward base 51 of body 50 in an at least generally inward direction (corresponding to the out-of-plane direction in FIG. 3*a*), and that exhibit a ratio of their longest dimension to their shortest dimension, that is less than 10:1. In various embodiments, such columns may exhibit a longest/shortest dimension ratio that is less than about 8:1, 6:1, 4:1, 2:1, 1.5:1, or 1.2:1. In some embodiments this ratio may approach 1.0, e.g. such columns may exhibit relatively square cross-sectional appearances when viewed along the inward-outward axis of the earmuff.

Figure 5:
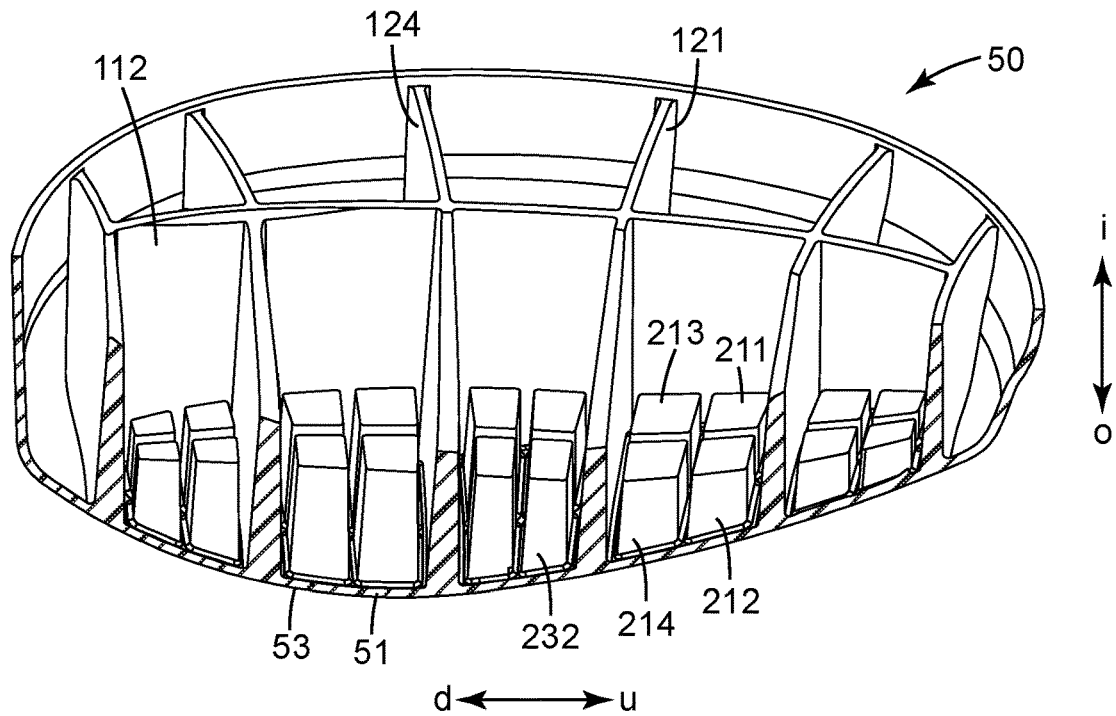
FIG. 5 is a front cross-sectional perspective view of an exemplary non-porous, sound attenuating body.
Figure 6:
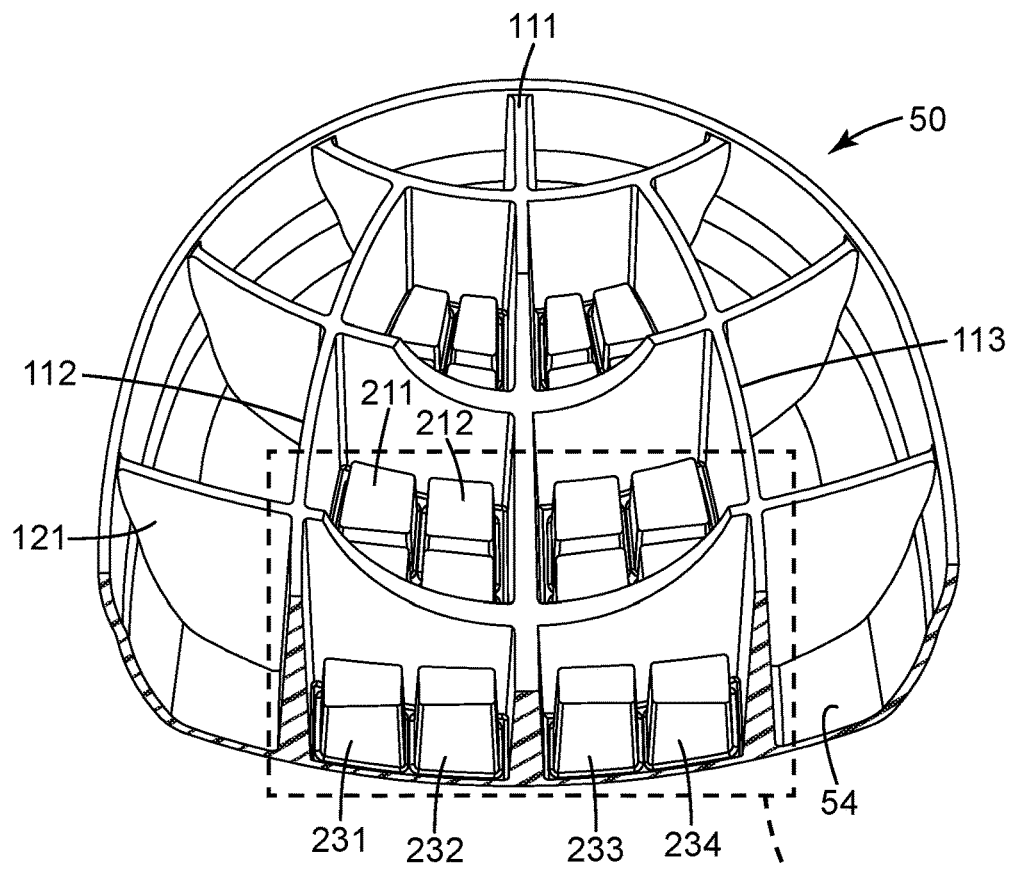
FIG. 6 is a bottom cross-sectional perspective view in cutaway of an exemplary non-porous, sound attenuating body.
Figure 7:
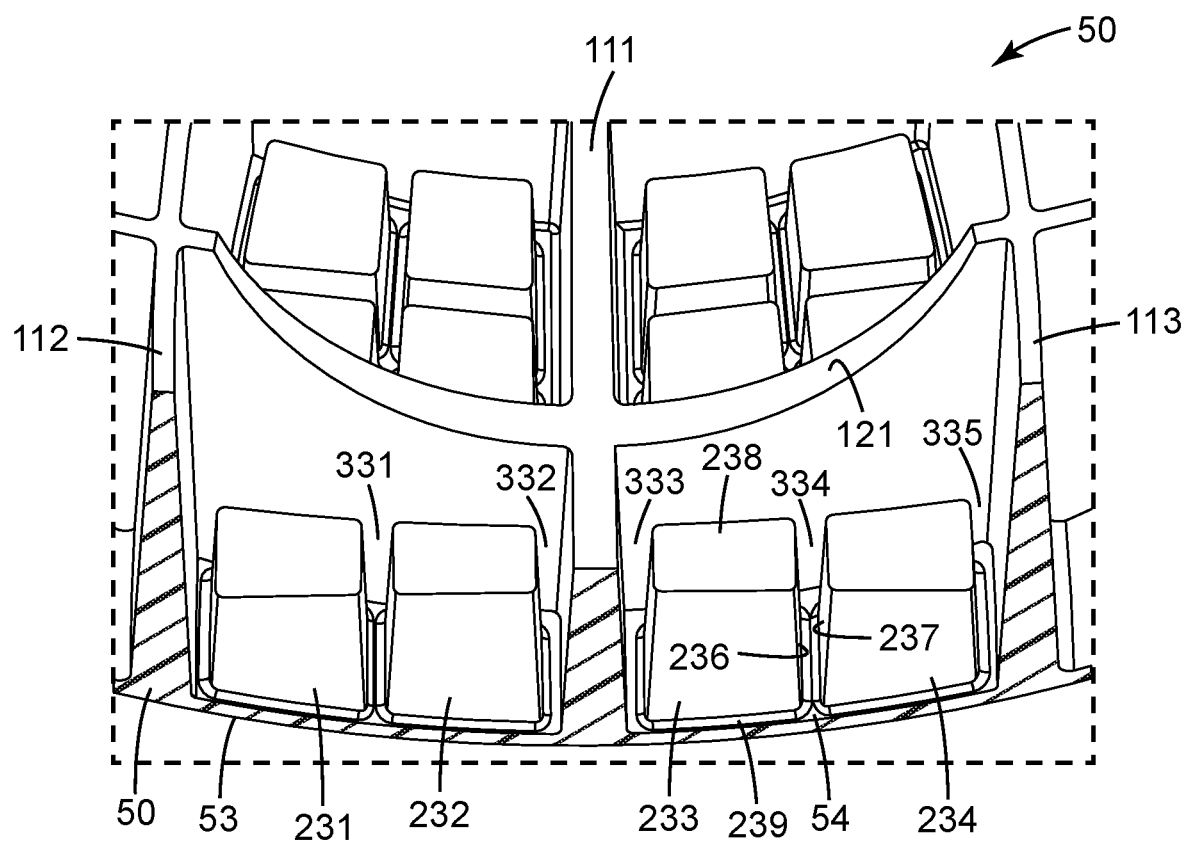
FIG. 7 is a magnified view of a portion of the exemplary non-porous, sound attenuating body of FIG. 6.

In some embodiments, at least some columns comprise major side surfaces, meaning sidewall surfaces that face e.g. generally longitudinally or laterally or any direction therebetween. FIGS. 5 and 6 present cross-sectional views taken at various angles and directions so that the design and features of exemplary columns, e.g. major side surfaces thereof, can be easily appreciated. FIG. 7 is a magnified view of a portion of FIG. 6 so that even more details can be distinguished. An exemplary major side surface 236 of column 233 and an exemplary major side surface 237 of column 234 are identified in FIG. 7; such major side surfaces are distinguished from inward surfaces of columns (e.g. from inward surface 238 of column 233). In some embodiments, at least some columns may comprise at least three major side surfaces (for examples, columns may be present as an array of columns that each exhibit a triangular cross-section). In some embodiments at least some columns may comprise four major side surfaces, e.g. so that the columns take the form of generally cuboid-shaped bodies (e.g. as shown in FIGS. 5-6 and as shown in magnified view in FIG. 7) with four side walls, each bearing a major side surface, and with one inward major surface. In some embodiments at least some columns many comprise more than four major side surfaces, e.g. they may take the form of hexagonal posts. It will be appreciated that some such columns may thus take the form of polygonal posts with any desired number of major side surfaces; in some embodiments, some such columns may take the form of cylindrical posts, annular posts, or the like, as will be discussed later herein. In some embodiments at least some columns may be solid bodies that do not comprise any cavities or hollow spaces within their interiors. (In some embodiments, at least some elongated ribs as described above, may also be solid bodies.)

In some embodiments at least some columns may be inwardly-tapered as most clearly visible in the magnified view of FIG. 7. By inwardly-tapered is meant that a column exhibits a cross-sectional area at an inward end of the column, that is smaller than the cross-sectional area at an outward "end" of the column (an outward "end" meaning the location at which the column joins inward surface 54 of outward base 51 of body 50). In relatively "flat-topped" columns e.g. of the type exemplified by column 233 of FIG. 7, the cross-sectional area of the inward end will be the area of inward surface 238. The cross-sectional area of the outward end of column 233 will be the area of an imaginary slice taken through the column at the location at which it joins inward surface 54 of outward base 51 of body 50 (e.g., the location identified by reference numeral 239 in FIG. 7). In various embodiments, some columns may be inwardly tapered so as to exhibit a ratio of an inward-end cross-sectional area to an outward-end cross-sectional area, of less than about 0.95, 0.9, 0.8, 0.7, or 0.6. In further embodiments, at least some columns may be inwardly tapered so as to exhibit such a ratio of at least about 0.2, 0.4, 0.6, or 0.8. Any elongated rib or ribs may likewise be tapered at least in their "width" dimension, as is evident from inspection of rib 111 as shown in FIG. 7.

In many embodiments, the set of sound-attenuating members 100 of body 50 may be present as an array. Such an array may be regular or irregular, and if at least generally regular may have any suitable repeating configuration (for example, columns might be present e.g. as a triangular array of triangular posts, as a rectangular array of rectangular posts, as a hexagonal array of hexagonal posts, and so on). Such an array may include any desired number of columns, for example, from at least about 4, 8, 16, 32, or 64, to at most about 120, 100, 80, 60, 50, 40, or 30. By way of specific example, the exemplary design of FIG. 3*a* depicts an array of 40 columns (with columns 211-214, 221-224, and 231-232 being individually numbered). In the embodiment of FIG. 3*a* the columns are in groups of four, each group occupying a compartment defined by elongated ribs. For example, columns 221-224 occupy compartment 132 defined by longitudinal ribs 111 and 113 and lateral ribs 124 and 125. Any number of compartments and columns therein, may be used as desired.

It may be convenient to characterize a set (e.g. an array) of columns by way of the relationship between neighboring columns. It will be understood that neighboring columns are those that have no portion of any other column (or elongated rib) between them and that have major side surfaces that at least generally face each other (e.g. within an angle of about 40, 30, 20 or 10 degrees). By way of specific example with reference to FIG. 3*a*, columns 211 and 214 are each a neighboring column to column 212; however, columns 211 and 214 are not neighboring columns to each other.

For reasons which will be clear from later discussions, it can be advantageous to space such columns in a close-packed array so that the spaces between major side surfaces of neighboring columns take the form of high aspect ratio air gaps. Thus in various embodiments, at least some columns may be arranged and spaced so that a column exhibits a center-to-center spacing with a neighboring column, that is greater than an edge-to-edge spacing with that neighbor column, by a factor of at least about four. By way of specific example, an edge-to-edge spacing between columns 233 and 234 as shown in FIG. 7 will be the (average) distance between major side surface 236 of column 233 and major side surface 237 of column 234. In some embodiments, many or all such columns may exhibit a center-to-center to edge-to-edge spacing factor of at least about 4. In further embodiments, such a spacing factor for some or all columns may be at least about six, eight, or ten. The arrangement and spacing of columns may also be characterized by the ratio of the volume occupied by two neighboring columns to the volume occupied by air in the gap between the two columns. By way of specific example, the total volume of columns 233 and 234 (not counting the volume of the portion of base 51 that outwardly borders these columns) can be divided by the volume of the air gap (denoted by reference number 334 in FIG. 7) between major side surfaces 236 and 237 of these columns. In various embodiments, such a volumetric ratio may be at least about 4:1, 6:1, 8:1, 10:1, 15:1, 20:1, 30:1, or 40:1.

It has been found that providing inwardly-extending members (e.g. in the form of columns, along with at least some elongated ribs if desired) as described herein can advantageously enhance the attenuation of undesirable sound within an earmuff. This can be accomplished by any number of mechanisms, any one or more of which may be operative in a given sound field. Specifically, it has been found that providing solid surfaces (e.g. major side surfaces of sound-attenuating members of body 50) in close proximity to each other can provide a high aspect ratio (e.g. deep and narrow) air gap 300, e.g. a closed-end air gap, that can absorb at least some airborne sound e.g. through frictional or visco-thermal effects. In other words, sound waves that enter and propagate down such an air gap may undergo large frictional losses against the major side surfaces that define the gap. The provision of a number of members, arranged as indicated herein, can thus achieve significant sound absorption and can "scavenge" airborne sound in interior space 31 of shell 30 of earmuff 20. This means, for example, that at least some sound waves that may leak in between cushion 40 and the side of the wearer's head, and/or at least some sound waves that may penetrate directly through shell 30, may be absorbed by the action of the high aspect ratio air gaps of body 50 before these airborne sound waves can enter the ear canal of the user. It will be appreciated that such high aspect ratio air gaps can be provided not just between major side surfaces of columns, but also between a major side surface of a column and a major side surface of an elongated rib, to similar effect. Such high aspect ratio air gaps can also be provided between major side surfaces of two neighboring ribs, if desired.

Thus in various embodiments, a set of inwardly-extending members (whether e.g. columns, ribs, or both) can be arranged and spaced so that a set of high aspect ratio air gaps 300 is present between major side surfaces of at least some neighboring members. By a high aspect ratio air gap is meant an air gap, between major side surfaces of neighboring members, that exhibits an average width, between the major side surfaces of the members, of no more than 3.0 mm. By way of a specific example, the width of air gap 334 of FIG. 7 will be the distance between major side surface 236 of column 233 and major side surface 237 of column 234. (In a case in which the columns are tapered, as in FIG. 7, this distance can be averaged e.g. over the inward-outward extent ("depth") of the air gap.) In various embodiments, a high aspect ratio air gap as disclosed herein may exhibit an average width of no more than about 2.5, 2.0, 1.5, or 1.0 mm. By a high aspect ratio air gap is also meant an air gap that exhibits a ratio of depth to (average) width, over the extent (depth) of the air gap that has a local width of 3.0 mm or less, of at least about 5:1. By way of a specific example, the depth of air gap 334 as depicted in FIG. 7, is the distance from inward surface 54 of base 51 at a location between columns 233 and 234, to a location even with inward surface 238 of column 233. If a column is present that is e.g. tapered sharply toward its inward end, the inward "end" of the column for the purposes of calculating an aspect ratio for an air gap between a major side surface of that column and that of a neighboring column or rib, may be taken as the location, along the inward-outward axis of the column, at which that major side diverges from the major side surface of the neighboring column or rib, a distance of more than 3.0 millimeters.

In various embodiments, an aspect ratio of an air gap between a major side surface of a column or rib, and a major side surface of a neighboring column or rib, can be at least about 6:1, 8:1, 10:1, 12:1, 15:1, or 20:1 (with averages of depths and/or widths being used if needed e.g. for tapering columns or for arrangements in which the air gap varies in some other way).

The specific geometric parameters (e.g. height along an inward-outward dimension, length, width and cross-sectional area) of columns (and elongated ribs) can be chosen as desired, as long as at least some high aspect ratio air gaps are provided. In some embodiments, the column heights may remain well below the heights of elongated ribs, as in the exemplary embodiments depicted in various Figures herein. In various embodiments, columns may exhibit heights of at least about 3, 4, 8, 12, or 15 mm; in further embodiments, columns may exhibit heights of at most about 30, 25, 20, or 16 mm. In various embodiments, columns may exhibit cross-sectional areas of at least 6, 10, 15, 20, 25, 30, 35, 40, 45 or 50 mm; in further embodiments, columns may exhibit cross-sectional areas of at most about 100, 90, 80, 70, 60, 50, or 40 mm. (For relatively flat-topped columns, such a cross-sectional area may be measured at an inward surface such as e.g. surface 238 of column 233 as shown in FIG. 7; for columns that e.g. taper sharply toward their inward end, a cross-sectional area may be measured at a height that corresponds to the major side surfaces of the column being a distance of 3.0 mm from the major side surfaces of neighboring columns and/or ribs.

While columns (and ribs) are depicted in the Figures herein as having relatively planar major side surfaces, such side surfaces may be non-planar (e.g. irregular, furrowed, scalloped, and so on). Moreover, side surfaces of major sides of neighboring columns and/or ribs need not be exactly parallel to each other, as long as a significant portion (e.g. greater than 30, 40, or 50%) of the side surfaces are within 3.0 mm of a neighboring side surface. In various embodiments a major side surface of a column or rib may be angled, on average, within 30, 20, 15, 10, 5, or 2 degrees of parallel to a nearest major side surface of a neighboring column or rib. Regardless of the exact angle and/or planarity of the major side surfaces, it will be appreciated that it is advantageous for major side surfaces of members (e.g. columns or elongated ribs) to be positioned sufficiently close to a major side surface of a neighboring member to provide high aspect ratio air gaps. Thus in various embodiments, at least about 20, 30, 40, 50, 60, 70, 80, or 90% of the total surface area of identifiable major side surfaces of columns of body 50, will be located within 3.0, 2.5, 2.0, 1.5, or 1.0 mm of major side surfaces of neighboring columns or elongated ribs.

Although certain exemplary designs have been discussed herein in detail, it is emphasized that sound-attenuating members 100 can have any suitable design as long as at least some high aspect ratio air gaps 300 are provided. For example, such members could be provided as a set of inwardly-extending, annular (e.g. concentric) structures (e.g. flanges, fins, or the like) 100 that define high aspect ratio air gaps 300 therebetween, as depicted in exemplary, generic representation embodiment in FIGS. 8a and 8b. While the term "annular" is used for convenience of description, it will be understood that such members do not necessarily need to be e.g. strictly circular, or oval, in shape when viewed along the inward-outward axis of body 50. Moreover, they may, but are not required to, exhibit any axis of symmetry in such a view. In some embodiments, rather than being smoothly curved as in the exemplary design of FIG. 8a, such members may exhibit polygonal shapes in which surfaces of inward-facing segments of one member, and surfaces of outward-facing segments of another member, combine to form high aspect ratio air gaps, as in the exemplary design of FIG. 8b. Mixtures or combinations of segments with smoothly curving surfaces and planar surfaces may be used as desired. It will be understood that any such members may e.g. qualify as ribs, or as columns, as described herein, depending e.g. on the particular dimensions of the members.

Although primarily discussed so far in terms of distances between major side surfaces of neighboring columns, high aspect ratio air gaps can be provided between major side surfaces of columns and major side surfaces of neighboring elongated ribs, or between major side surfaces of elongated ribs that neighbor each other. The above-discussed values for aspect ratios and other parameters may be applied to such arrangements in similar manner. From the above discussions it will be appreciated that providing high aspect ratio air gaps can advantageously promote the effects disclosed herein. It will also be appreciated that arrangements in which minor edges/surfaces (rather than major side surfaces) of items such as partitions or walls are positioned near major side surfaces of neighboring items do not provide high aspect ratio air gaps between major side surfaces of the type disclosed herein. One example of arrangements that will be recognized by ordinary artisans as not providing high aspect ratio air gaps between major side surfaces as disclosed herein, is the system of partitioning walls disclosed in PCT Published Application WO 94/17763.

It has also been found that inwardly-extending members (e.g. columns) as disclosed herein may achieve sound absorption other than merely by promoting frictional (e.g. thermoacoustic) sound dissipation within high aspect ratio air gaps between major side surfaces of the members. Specifically, it appears that such columns may be able to be set at least slightly in motion by airborne sound within interior space 31 of shell 30. Such columns may comprise e.g. size, shape, stiffness, density, and so on, so as to exhibit a resonant frequency at which the columns may be set in motion, that lies within the audible range. Such columns may thus be set in motion by airborne sound and at least some portion of the sound energy may then be dissipated by way of internal frictional effects (e.g. viscoelastic losses)

within the material of the columns. In other words, the columns may be acting somewhat like tuned resonant absorbers. While tuned resonant absorbers are usually thought of as being formulated from plates of a relatively rigid material (e.g. metal) to which is affixed a slab of material with specifically chosen viscoelastic properties (e.g. a layer of soft, gummy material with a very high loss modulus), the present work has indicated that columns as described herein, even when comprised of monolithic pieces of e.g. injection-molded plastic, can exhibit such an effect to an extent to contribute usefully to sound attenuation.

It has still further been found that providing some inwardly-extending members in the form of elongated ribs can have advantageous effects beyond the effects described above. Specifically, such elongated ribs can address the problem that in some cases "rigid" shells as conventionally used in earmuffs of hearing-protection devices can undesirably transmit at least some sound therethrough by direct transmission. That is, at least at some frequencies, at least a portion of a shell 30 may be set into motion by airborne sound that strikes the outward surface of the shell. The motion of this portion of the shell may then cause airborne sound waves to be emitted into interior 31 of the shell. (This ability of such shells to vibrate to a sufficient extent to transmit sound therethrough at least at some frequencies, is why such shells 30 as discussed herein are referred to as being "substantially" rigid rather than rigid, as it appears that such shells are sometimes able to flex and vibrate to at least a slight extent.)

Upon this realization, it was found that providing a body 50 that comprises elongated ribs (e.g. a first set of longitudinal ribs and a second set of lateral ribs) and closely abutting such a body against inward surface 34 of shell 30, may reduce undesirable transmission of sound through portions of shell 30. It will thus be appreciated that in some cases elongated ribs may serve to minimize transmission of solid-borne sound. It was already noted that if such ribs are provided with major side surfaces, these can provide (e.g. in combination with major side surfaces of neighboring columns, or with major side surfaces of neighboring ribs) high aspect ratio air gaps that promote absorption of airborne sound through the mechanisms discussed earlier herein. It will thus be evident that some ribs may serve primarily to minimize transmission of solid-borne sound, some such ribs may serve primarily to enhance absorption of airborne sound, and some ribs may serve both functions. It will also be appreciated that in any given sound field the relative contribution of the various sound-attenuating mechanisms discussed above may vary.

It will be appreciated from the above discussions that a sound-attenuating body 50 as disclosed herein can advantageously reduce the amount of sound that reaches the ear canal of a wearer of an earmuff hearing-protection device, by any or all of several sound-attenuation mechanisms. Moreover, it has been found that this can be done without the necessity of body 50 being made from, or including, a porous sound-absorbing material of the type conventionally used inside the interior of shells of hearing-protection earmuffs. Still further, it has been found that the inclusion of a sound-attenuating body 50 within an interior space of an earmuff shell as disclosed herein can allow sufficiently high performance (e.g. as manifested by an Insertion Loss of a desired value in a frequency range of interest, and/or as characterized by a desired SNR) that little or no conventional porous sound-absorbing material (e.g., fiberglass, foam rubber, non-woven organic polymeric fibrous material, and so on) need be present, if this is desired. Thus in various embodiments, less than 20, 10, 5, 2, or 1% of the total volume of interior space 31 of a shell 30 of an earmuff 20 as disclosed herein, may be occupied by porous sound-absorbing material. In some embodiments, interior space 31 may be essentially free of any such porous sound-absorbing material. However, in some embodiments a porous sound-absorbing material may be present (and e.g. may occupy at least about 2, 5, 10, 20, or 40% of the total volume of interior space 31).

It will be appreciated that the ability to reduce (e.g. to completely omit) conventional porous sound-absorbing material from the interior of a shell of an earmuff can advantageously provide that the earmuff is less susceptible to e.g. retention of moisture. This can allow that an earmuff can be easily washed (e.g. can be put into an automatic dishwasher) without the necessity of removing conventional porous sound-absorbing material from the earmuff (although any ear-encircling cushion may be removed if desired). The earmuff may also be e.g. more durable and less susceptible to damage or wear and tear.

It is noted that in some embodiments an earmuff 20 may include a screen that inwardly overlies interior space 31 of shell 30. For example, such a screen might have perimeter edges that are captured between rim 33 of shell 30, and an outward end of cushion 40, to hold the screen in place. Such a screen may be primarily cosmetic or aesthetic (e.g. it may serve to hide interior space 31 of shell 30 from view rather than performing e.g. any significant sound-absorbing function. Such a screen may also serve to prevent macroscopic debris from entering interior space 31 of shell 30. Such a screen, if present may be comprised of e.g. a woven or non-woven layer, a perforated film, a reticulated netting, and so on. In some embodiments, no such screen of any kind is present.

Although body 50 and sound-attenuating members thereof have been primarily discussed in terms of body 50 being made separately from shell 30 and then e.g. inserted thereinto, in some embodiments body 50 may be molded as a part of shell 30. That is, in some embodiments shell 30 and body 50, including e.g. inwardly-extending columns and/or elongated ribs thereof, may be molded as a single, unitary, integral piece. In other embodiments, shell 30 and body 50 may be provided as co-molded pieces achieved e.g. by co-injection molding. In some embodiments the inward face of shell 30 may comprise one or more mating features to which sound-attenuating members 100 (whether columns or ribs) may be attached by use of complementary mating features present on the outward ends of one or more of the members. For example, the inward face of shell 30 might comprise a set of inwardly-protruding posts, onto which sound-attenuating members 30, one or more of which comprise at least one outward-facing cavity that is complementary with a shell post, can be attached e.g. by snapping, e.g. in the manner of the well-known products available under the trade designation LEGOS. In any such arrangement of this type shell 30 itself will be considered to provide outward base 51 of sound-attenuating body 50. Any suitable method of attaching such members (e.g. mechanical attachment, adhesive bonding, ultrasonic bonding, and so on) to shell 30 may be used. Any such arrangement can allow shell 30 and body 50, and/or shell 30 and sound-attenuating members 100, to be made of different organic polymeric materials, each chosen to have suitably optimum properties as desired.

In some embodiments, an earmuff hearing-protection device 1 as disclosed herein (including a sound-attenuating body 50) may be sold as part of a kit. Such a kit may include one or more earmuff hearing-protection devices 1, and might further include one or more replacement bodies 50, replacement cushions 40, and so on. In some embodiments such a kit may include instructions for use, whether e.g. printed on packaging that device 1 is packaged in, printed on a paper insert that is included in the packaging, or printed on a surface of a component of device 1. Such instructions encompass virtual instructions, meaning instructions that are stored at a publically-accessible website, with the kit including (e.g. whether printed on an insert, on the packaging, or on the actual product) a statement directing a user to the website to obtain the instructions. Regardless of the specific format, in some embodiments such instructions for use of the device will include instructions for care and cleaning of the device; in specific embodiments, such instructions for cleaning will include a step of cleaning an earmuff of the device but will not include any step directing the user to remove any porous sound-absorbing material from an interior space of the shell of the earmuff before cleaning the earmuff.

List of Exemplary Embodiments

Embodiment 1 is an earmuff hearing-protection device comprising: a headpiece; a pair of earmuffs affixed to the headpiece, each earmuff comprising a generally cup-shaped, substantially rigid shell that defines an interior space and that comprises a head-facing inward rim; a head-engaging, ear-encircling sealing ring affixed to the inward rim of the shell; and, a non-porous, sound-attenuating body disposed within the interior space defined by the shell, wherein the non-porous, sound-attenuating body comprises an outward base and a set of sound-attenuating members that extend at least generally inwardly from the outward base, with at least some of the inwardly-extending, sound-attenuating members being arranged and spaced so as to define a set of high aspect ratio air gaps between major side surfaces of neighboring members.

Embodiment 2 is the device of embodiment 1 wherein at least some of the sound-attenuating members are arranged and spaced so as to define a set of high aspect ratio air gaps with an aspect ratio of at least about 8:1 between major side surfaces of neighboring members.

Embodiment 3 is the device of embodiment 1 wherein at least some of the sound-attenuating members are arranged and spaced so as to define a set of high aspect ratio air gaps with an aspect ratio of at least about 10:1 between major side surfaces of neighboring members.

Embodiment 4 is the device any of embodiments 1-3 where at least some of the sound-attenuating members are in the form of inwardly-extending columns that exhibit at least three major side surfaces, at least two of which major side surfaces each define a high aspect ratio air gap between that major side surface and a major side surface of a neighboring member.

Embodiment 5 is the device of any of embodiments 1-4 wherein at least some of the sound-attenuating members are in the form of inwardly-extending columns are that are generally cuboid-shaped bodies that exhibit four major side surfaces, each of which major side surfaces defines a high aspect ratio air gap between the major side surface and a major side surface of a neighboring member.

Embodiment 6 is the device of any of embodiments 4-5 wherein at least some of the inwardly-extending columns each exhibit a center-to-center spacing with a neighboring column that is greater than an edge-to-edge spacing with the neighboring column by a factor of at least about four.

Embodiment 7 is the device of any of embodiments 4-6 wherein for at least some of the inwardly-extending columns, a ratio of the volume occupied by two neighboring columns to a volume occupied by air in a high aspect ratio air gap between the two neighboring columns is at least about 4:1.

Embodiment 8 is the device of any of embodiments 4-7 wherein at least about 70% of a total collective surface area of major side surfaces of inwardly-extending columns of the sound-attenuating body is located within 2.0 mm of major side surfaces of neighboring columns or of neighboring elongated ribs.

Embodiment 9 is the device of any of embodiments 4-8 wherein at least some of the inwardly-extending columns are tapered so as to exhibit an area at an inward end of the column, that is from about 0.6 to about 0.95 of an area of an outward end of the column at a location at which the column joins a major inward surface of the outward base of the sound-attenuating body.

Embodiment 10 is the device of any of embodiments 4-9 wherein at least some of the inwardly-extending columns are solid columns so that no cavity or cavities are present within the interiors of the columns.

Embodiment 11 is the device of any of embodiments 1-10 wherein at least some members of the set of sound-attenuating members that extend at least generally inwardly from the outward base with at least some of the inwardly-extending, sound-attenuating members being arranged and spaced so as to define a set of high aspect ratio air gaps between major side surfaces of neighboring members, are in the form of elongated ribs.

Embodiment 12 is the device of embodiment 11 wherein the elongated ribs include a first set of longitudinal ribs and a second set of lateral ribs, each longitudinal rib intersecting at least two lateral ribs and each lateral rib intersecting at least two longitudinal ribs.

Embodiment 13 is the device of embodiment 12 wherein the first set of longitudinal ribs and the second set of lateral ribs collectively define a set of compartments that are each bounded by two longitudinal ribs and two lateral ribs, and wherein at least some compartments of the set of compartments defined by the ribs are occupied by at least two inwardly-extending, sound-attenuating members that are in the form of inwardly-extending columns.

Embodiment 14 is the device of any of embodiments 12-13 wherein at least some ribs of the first set of longitudinal ribs are arcuate and convex with respect to a longitudinal centerline of the non-porous, sound-attenuating body, and wherein at least some ribs of the second set of lateral ribs are arcuate and concave with respect to a lateral centerline of the non-porous, sound-attenuating body.

Embodiment 15 is the device of any of embodiments 12-14 wherein at least some of the elongated ribs include portions that extend further inward than any portion of any column extends inward, and further wherein at least some of the ribs each exhibit an outwardly-concave profile with a maximally-outward location of an inward surface of each rib being located proximate a centerline of the non-porous, sound-attenuating body.

Embodiment 16 is the device of any of embodiments 1-15 wherein an outward surface of the outward base of the non-porous, sound-attenuating body exhibits a shape that is at least substantially congruent with an inward surface of the substantially rigid shell and wherein portions of the outward base of the non-porous, sound-attenuating body extend inwardly to provide an inward rim of the non-porous, sound-attenuating body.

Embodiment 17 is the device of any of embodiments 1-16 wherein the non-porous, sound-attenuating body, including the outward base and at least some sound-attenuating members of the set of sound-attenuating members that extend at least generally inwardly from the outward base, is a unitary, integral piece of molded organic polymeric resin.

Embodiment 18 is the device of any of embodiments 1-17 wherein less than 5% of the volume of the interior space defined within the substantially rigid shell of the earmuff is occupied by porous sound-absorbing material.

Embodiment 19 is the device of any of embodiments 1-17 wherein less than 2% of the volume of the interior space defined within the substantially rigid shell of the earmuff is occupied by porous sound-absorbing material.

Embodiment 20 is the device of any of embodiments 1-19 wherein the non-porous, sound-attenuating body that is disposed within the interior space defined by the substantially rigid shell, is a separately-made piece from the shell, the separately-made sound-attenuating body being disposed within the shell so that an outward surface of the outward base of the sound-attenuating body is abutted against an inward surface of the substantially rigid shell.

Embodiment 21 is the device of any of embodiments 1-20 wherein the sound-attenuating body is non-detachably attached to the substantially rigid shell.

Embodiment 22 is the device of any of embodiments 1-20 wherein the sound-attenuating body is detachable from the substantially rigid shell and is removable from the interior space defined by the substantially rigid shell.

Embodiment 23 is the device of any of embodiments 1-15, 17-19, and 21 wherein the sound-attenuating body and the substantially rigid shell are portions of a single, integral piece of molded plastic.

Embodiment 24 is the device of any of embodiments 1-23 wherein each earmuff is removably affixed to the headpiece.

Embodiment 25 is the device of any of embodiments 1-24 wherein the headpiece is chosen from the group consisting of a resilient headband, and a hardhat.

Embodiment 26 is a kit comprising at least one earmuff hearing-protection device of any of embodiments 1-25, the kit including instructions and/or virtual instructions for cleaning the device, the instructions including a step of cleaning an earmuff of the device but not including a step of removing porous sound-absorbing material from the interior of the substantially rigid shell before cleaning the earmuff of the device.

Examples

Production of Working Example Sound-Attenuating Bodies

Prototype sound-attenuating bodies were formulated using a material obtained under the trade designation ALCHEMIX VC 332 from Alchemie Ltd. (Kineton, UK). This material was a two-part polyurethane molding resin reported by the supplier to provide (after curing) a flexible polyurethane product with a Shore A hardness in the range of 60-65. The bodies were sized and shaped to form "inserts" that could fit snugly into interior spaces of shells of earmuff hearing-protection devices available from 3M Company under the trade designation 3M PELTOR OPTIME II Ear Muffs. The inserts were substantially of the design depicted in the Figures herein, comprising forty inwardly-extending columns in groups of four, each group of four being provided within a compartment defined by longitudinal ribs and lateral ribs in the manner depicted e.g. in FIG. 3a. The majority of the columns were configured so that the air gap distances between major side surfaces of neighboring columns were in the range of approximately 0.8 mm at the bases of the columns, and in the range of approximately 1.5 mm at the tops (the inwardmost surfaces) of the columns. The column heights varied thus the depths of the various air gaps likewise varied (within a range of approximately 5 mm to 12 mm). The aspect ratios of the air gaps were believed to be within a range of approximately 5:1 to 15:1. The major side surfaces were essentially planar so that the distances between the major side surfaces of neighboring columns varied smoothly along the height of the columns. The distances between major side surfaces of columns and major side surfaces of neighboring elongate ribs were similarly configured. The inserts had elongate ribs substantially as depicted in the Figures herein.

Insertion Loss

Earmuff hearing-protection products, comprising shells, ear-encircling sealing rings (cushions), and headbands, of the type used in 3M PELTOR OPTIME II Ear Muffs but not comprising any conventional porous sound-absorbing material within the interior spaces of the shells, were obtained. (OPTIME II Ear Muffs as commercially supplied customarily include porous sound-absorbing material in the form of slabs of sound-absorbing foam within the interior spaces of the shells.) The inserts were individually inserted into the OPTIME shells, whereupon the inserts fit snugly within the interior spaces of the shells with the outward surfaces of the inserts closely abutting the inward surfaces of the shells. The inserts were attached to the OPTIME II shells by thin layers of adhesive that were disposed between the outward surfaces of the inserts and the inward surfaces of the shells. The adhesive was a two-part epoxy obtained from 3M Company (St. Paul, Minn.) under the trade designation SCOTCH-WELD DP 490; the adhesive was applied to the inward surface of each shell with a glue gun and was then spread over the inward surface with a brush.

Comparative Example earmuffs were produced that used the above-described OPTIME II components, but that did not include inserts, or any conventional porous sound-absorbing material (e.g. foam slabs), within the interior spaces of the shells. Reference Example earmuffs were obtained in the form of off-the-shelf OPTIME II Ear Muffs that included slabs of sound-absorbing foam within the interior spaces of the shells.

Figure 9:
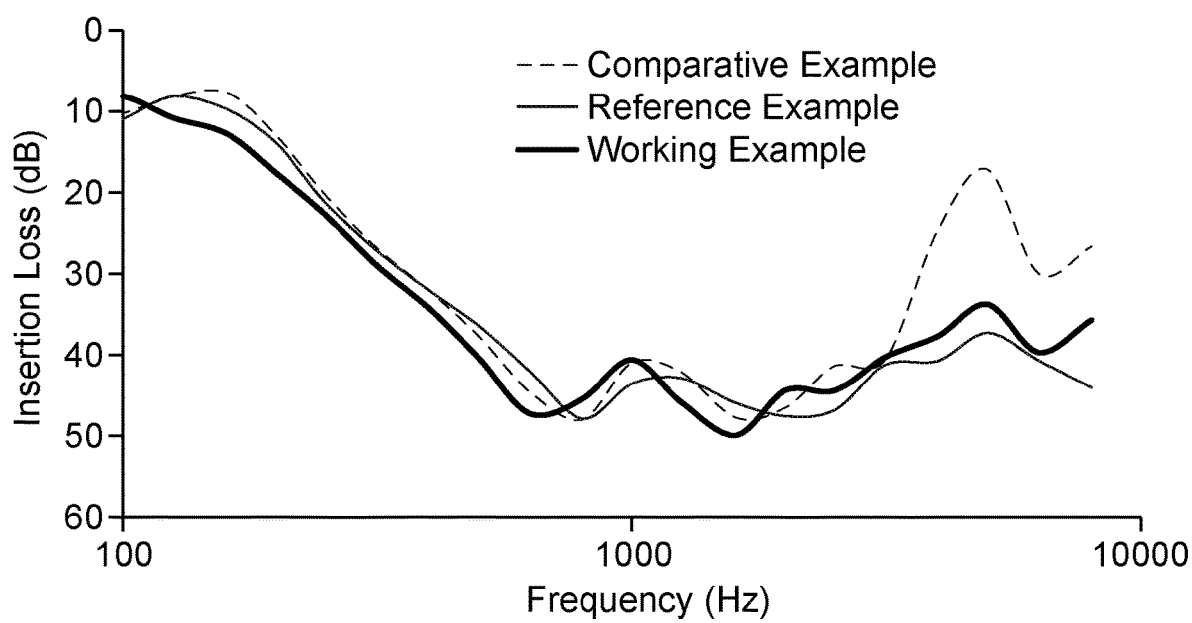
FIG. 9 presents Insertion Loss data for Working Examples.

The Working Example, Comparative Example, and Reference Example earmuff hearing-protectors were tested for Insertion Loss using a Type 45CA Hearing-protector Test Fixture of the type available from G.R.A.S. (Holte, Denmark). The results of the Insertion Loss testing are presented in FIG. 9.

Single Number Rating (SNR) testing

Working Example prototypes were produced as described above, with the molded inserts being adhesively bonded to the shells. Additional Working Example prototypes were also produced in which the molded inserts were not attached to the shells (rather, they were held in place by the ear-encircling cushions that were attached to the inward rims of the shells).

The thus-produced earmuffs were tested for Single Number Rating (SNR) in general accordance with the methods outlined in ISO Standard 4869-2. Each type of Working Example prototype (those with "unattached" inserts, and those with adhesively-attached inserts) was tested on at least eight human volunteers. For Working Examples with unattached inserts, an average SNR of 31 dB was obtained. For Working Example with adhesively-attached inserts, an average SNR of 31 dB was obtained. Reference Example earmuffs as described above (OPTIME II Ear Muffs comprising conventional porous sound-absorbing materials (foam slabs) within the interior spaces of the shells) were also evaluated, and exhibited an average SNR of 32 dB.

The foregoing Examples have been provided for clarity of understanding only, and no unnecessary limitations are to be understood therefrom. The tests and test results described in the Examples are intended to be illustrative rather than predictive, and variations in the testing procedure can be expected to yield different results. All quantitative values in the Examples are understood to be approximate in view of the commonly known tolerances involved in the procedures used.

It will be apparent to those skilled in the art that the specific exemplary elements, structures, features, details, configurations, etc., that are disclosed herein can be modified and/or combined in numerous embodiments. All such variations and combinations are contemplated by the inventor as being within the bounds of the conceived invention, not merely those representative designs that were chosen to serve as exemplary illustrations. Thus, the scope of the present invention should not be limited to the specific illustrative structures described herein, but rather extends at least to the structures described by the language of the claims, and the equivalents of those structures. Any of the elements that are positively recited in this specification as alternatives may be explicitly included in the claims or excluded from the claims, in any combination as desired. Any of the elements or combinations of elements that are recited in this specification in open-ended language (e.g., comprise and derivatives thereof), are considered to additionally be recited in closed-ended language (e.g., consist and derivatives thereof) and in partially closed-ended language (e.g., consist essentially, and derivatives thereof). Although various theories and possible mechanisms may have been discussed herein, in no event should such discussions serve to limit the claimable subject matter. To the extent that there is any conflict or discrepancy between this specification as written and the disclosure in any document that is incorporated by reference herein but to which no priority is claimed, this specification as written will control.

What is claimed is:

1. An earmuff hearing-protection device comprising:
a headpiece;
a pair of earmuffs affixed to the headpiece, each earmuff comprising:
a generally cup-shaped, substantially rigid shell that defines an interior space and that comprises a head-facing inward rim;
a head-engaging, ear-encircling sealing ring affixed to the inward rim of the shell;
and,
a non-porous, sound-attenuating body disposed within the interior space defined by the shell,
wherein the non-porous, sound-attenuating body comprises an outward base and a set of sound-attenuating members that extend at least generally inwardly from the outward base, with at least some of the inwardly-extending, sound-attenuating members being arranged and spaced so as to define a set of high aspect ratio air gaps between major side surfaces of neighboring members,
and wherein at least some of the sound-attenuating members are in the form of inwardly-extending columns that exhibit at least three major side surfaces, at least two of which major side surfaces each define a high aspect ratio air gap between that major side surface and a major side surface of a neighboring member.

2. The device of claim 1 wherein at least some of the sound-attenuating members are arranged and spaced so as to define a set of high aspect ratio air gaps with an aspect ratio of at least about 8:1 between major side surfaces of neighboring members.

3. The device of claim 1 wherein at least some of the inwardly-extending columns each exhibit a center-to-center spacing with a neighboring column that is greater than an edge-to-edge spacing with the neighboring column by a factor of at least about four.

4. The device of claim 1 wherein for at least some of the inwardly-extending columns, a ratio of the volume occupied by two neighboring columns to a volume occupied by air in a high aspect ratio air gap between the two neighboring columns is at least about 4:1.

5. The device of claim 1 wherein at least about 70% of a total collective surface area of major side surfaces of inwardly-extending columns of the sound-attenuating body is located within 2.0 mm of major side surfaces of neighboring columns or of neighboring elongated ribs.

6. The device of claim 1 wherein at least some of the inwardly-extending columns are tapered so as to exhibit an area at an inward end of the column, that is from about 0.6 to about 0.95 of an area of an outward end of the column at a location at which the column joins a major inward surface of the outward base of the sound-attenuating body.

7. The device of claim 1 wherein at least some members of the set of sound-attenuating members that extend at least generally inwardly from the outward base with at least some of the inwardly-extending, sound-attenuating members being arranged and spaced so as to define a set of high aspect ratio air gaps between major side surfaces of neighboring members, are in the form of elongated ribs.

8. The device of claim 7 wherein the elongated ribs include a first set of longitudinal ribs and a second set of lateral ribs, each longitudinal rib intersecting at least two lateral ribs and each lateral rib intersecting at least two longitudinal ribs.

9. The device of claim 1 wherein an outward surface of the outward base of the non-porous, sound-attenuating body exhibits a shape that is at least substantially congruent with an inward surface of the substantially rigid shell and wherein portions of the outward base of the non-porous, sound-attenuating body extend inwardly to provide an inward rim of the non-porous, sound-attenuating body.

10. The device of claim 1 wherein the non-porous, sound-attenuating body, including the outward base and at least some sound-attenuating members of the set of sound-attenuating members that extend at least generally inwardly from the outward base, is a unitary, integral piece of molded organic polymeric resin.

11. The device of claim 1 wherein less than 5% of the volume of the interior space defined within the substantially rigid shell of the earmuff is occupied by porous sound-absorbing material.

12. The device of claim 1 wherein less than 2% of the volume of the interior space defined within the substantially rigid shell of the earmuff is occupied by porous sound-absorbing material.

13. The device of claim 1 wherein the non-porous, sound-attenuating body that is disposed within the interior space defined by the substantially rigid shell, is a separately-made piece from the shell, the separately-made sound-attenuating body being disposed within the shell so that an outward surface of the outward base of the sound-attenuating body is abutted against an inward surface of the substantially rigid shell.

14. The device of claim 13 wherein the sound-attenuating body is non-detachably attached to the substantially rigid shell.

15. The device of claim 13 wherein the sound-attenuating body is detachable from the substantially rigid shell and is removable from the interior space defined by the substantially rigid shell.

16. The device of claim 1 wherein the sound-attenuating body and the substantially rigid shell are portions of a single, integral piece of molded plastic.

17. The device of claim 1 wherein the headpiece is chosen from the group consisting of a resilient headband, and a hardhat.

18. A kit comprising at least one earmuff hearing-protection device of claim 1, the kit including instructions and/or virtual instructions for cleaning the device, the instructions including a step of cleaning an earmuff of the device but not including a step of removing porous sound-absorbing material from the interior of the substantially rigid shell before cleaning the earmuff of the device.

19. An earmuff hearing-protection device comprising:
a headpiece;
a pair of earmuffs affixed to the headpiece, each earmuff comprising:
　a generally cup-shaped, substantially rigid shell that defines an interior space and that comprises a head-facing inward rim;
　a head-engaging, ear-encircling sealing ring affixed to the inward rim of the shell;
　and,
　a non-porous, sound-attenuating body disposed within the interior space defined by the shell,
　　wherein the non-porous, sound-attenuating body comprises an outward base and a set of sound-attenuating members that extend at least generally inwardly from the outward base, with at least some of the inwardly-extending, sound-attenuating members being arranged and spaced so as to define a set of high aspect ratio air gaps between major side surfaces of neighboring members,
　　and wherein at least some of the sound-attenuating members are in the form of inwardly-extending columns that are generally cuboid-shaped bodies that exhibit four major side surfaces, each of which major side surfaces defines a high aspect ratio air gap between the major side surface and a major side surface of a neighboring member.

* * * * *